United States Patent [19]

Liu

[11] Patent Number: 4,897,376

[45] Date of Patent: Jan. 30, 1990

[54] PROCESS FOR PREPARING A CATALYST FOR OXIDATION OF ETHYLENE TO ETHYLENE OXIDE

[75] Inventor: Kindtoken H. Liu, Park Ridge, N.J.

[73] Assignee: Scientific Design Company, Inc., Little Ferry, N.J.

[21] Appl. No.: 212,304

[22] Filed: Jun. 27, 1988

[51] Int. Cl.$^4$ .......................... B01J 23/04; B01J 23/50
[52] U.S. Cl. ...................................... 502/347; 549/534
[58] Field of Search ................................ 502/347, 348

[56] References Cited

U.S. PATENT DOCUMENTS

| | | | |
|---|---|---|---|
| 4,555,501 | 11/1985 | Armstrong | 502/347 X |
| 4,663,303 | 2/1986 | Becker et al. | 502/170 |
| 4,760,042 | 7/1988 | Armstrong | 502/348 X |
| 4,774,222 | 9/1988 | Rashkin | 502/347 |

*Primary Examiner*—W. J. Shine
*Attorney, Agent, or Firm*—Kenneth H. Johnson

[57] ABSTRACT

An improved silver catalyst for the oxidation of ethylene with molecular oxygen is made by impregnating a support with a silver salt prepared by reacting a silver compound with a neo-acid, in a hydrocarbon solvent with the reaction completed under reflux conditions; drying and activating the resultant precatalyst by heating in air; thereafter impregnating the activated catalyst with an amount, 800 to 5000 wppm of alkali metal, preferably Cs, to deactivate the catalyst to form a catalyst precursor and heating the catalyst precursor at 450°–700° C. for 0.1 to 4.5 hours at a steady state in a substantially inert atmosphere to reactivate it.

18 Claims, No Drawings

PROCESS FOR PREPARING A CATALYST FOR OXIDATION OF ETHYLENE TO ETHYLENE OXIDE

BACKGROUND OF THE INVENTION

1. Field of the Invention

The present invention relates generally to a supported silver catalyst useful for the vapor-phase oxidation of ethylene to ethylene oxide and the method of producing ethylene oxide. More particularly, the invention relates to a supported silver catalyst containing an alkali metal such as cesium. The present invention also relates to a method of preparing an improved supported silver catalyst containing such an alkali metal and exhibiting increased activity and selectivity.

2. Related Art

The use of supported silver catalysts for the oxidation of ethylene to ethylene oxide has been long known in the art. Additionally, over the years various promoting metals have been added to further enhance performance. In particular, the use of alkali metals has been disclosed in various amounts and added by different methods. A very extensive review of the patent literature is given in G.B. No. 2,043,481A. Such disclosures have been somewhat inconsistent in their teachings, as can be seen by comparing U.S. Pat. No. 2,238,474 in which sodium and lithium hydroxides were suggested as promoters and potassium and cesium were shown to be poisons to U.S. Pat. No. 2,671,764 where rubidium and cesium sulfates were suggested as promoting compounds.

Although alkali metals were suggested generally in the earlier disclosures, it is also generally true that more recent workers in the field have considered potassium, rubidium, and cesium as the preferred alkali metals. For example, see the series of patents to Nielson, et al., in which these materials were used in small amounts co-deposited with the silver—U.S. Pat. Nos. 3,962,136; 4,010,115; and 4,012,425. Still more recently the art has emphasized synergistic combinations of the alkali metals. For example see G.B. No. 2,043,241A cited above and U.S. Pat. Nos. 4,212,772 or 4,226,782. The art teaches, in addition that the alkali metals may be used to rejuvenate used catalysts, as for example U.S. Pat. Nos. 4,123,385; 4,033,903; 4,177,169; and 4,186,106. The art teaches that the alkali metals may be deposited either before the silver is placed on the support (pre-deposited)—U.S. Pat. No. 4,207,210; at the same time the silver is deposited (co-deposited)—U.S. Pat. Nos. 4,066,575 and 4,248,740; or subsequent to deposition of silver (post-deposited)—G.B. No. 2,045,636A.

The amount of alkali metal was suggested to be in quite a wide range in the older art. It was often indicated that large quantities, e.g. up to several per cent of an alkali metal could be used. More recently, the art generally has taught that small quantities of alkali metals produce the optimum effect no matter when the silver and the alkali metals were deposited. Kilty in U.S. Pat. No. 4,207,210 related the optimum amount to the surface area of the support. Exceptions to the above include patents issued to ICI which teach the use of large amounts of sodium alone (G.B. No. 1,560,480) and potassium in combination with smaller amounts of cesium and rubidium (U.S. Pat. No. 4,226,782). However, the art generally teaches that the optimum will be found in substantially lower quantities, perhaps on the order of 50–500 ppm by weight. An improved silver catalyst, prepared by impregnating a support with a hydrocarbon solution of a silver salt of a neo-acid having 7 or more carbon atoms is disclosed in commonly assigned U.S. Pat. No. 4,555,501 to Armstrong and subsequently modified by Becker et al in commonly assigned U.S. Pat. No. 4,663,303 both of which are incorporated herein in their entirety.

Commonly assigned U.S. patent application of Rashkin U.S. Pat. No. 4,774,222 teaches that large amounts of alkali metals might be used. However, "reactivation" at higher temperatures for considerable time periods is required. For example, the shortest time period used in the examples is three hours followed by an additional eleven hours although shorter periods are suggested. Likewise, Mitsuhata in U.S. Pat. No. 4,389,338 discloses the use of higher amounts of alkali metals and the "reactivation" at higher temperatures for lengthy periods. For example Mitsuhata requires 12 hours of heat treatment at 600° C.

It has now been found that if the procedure of the present invention is followed, the high temperature treatment period can be reduced significantly, e.g., two hours at 600° C. in lieu of the 12 hours required by Mitsuhata and similar periods used by Rashkin and the catalyst produced may be more stable than the neo-acid catalysts of Armstrong and Becker, et al.

SUMMARY OF THE INVENTION

Briefly stated one aspect of the present invention is a catalyst prepared by the process of impregnating a porous support having a low surface area with a hydrocarbon solution of a silver salt of a neo-acid which is substantially free of water and neo-acid, heating the impregnated support to produce an active catalyst, further impregnating the active catalyst with a solution of alkali metal salt in an amount to deactivate said catalyst and thereafter heating said deactivated catalyst at a temperature of at least 450° C. to preferably about 700° C. for a sufficient period of time in a substantially inert atmosphere to activate said catalyst. The process of preparing the catalyst and the preparation of ethylene oxide using the catalyst are other aspects of the present invention.

In a particular aspect of the present invention it has been found that silver catalyst prepared by impregnating a suitable support with a hydrocarbon solution of a silver salt of a neo-acid having 7 or more carbon atoms produces a preferred catalyst. The thus prepared silver catalyst is activated in air as described and then according to the present invention, it is treated with solution of an alkali metal compound in an amount sufficient to depress the activity and selectivity of the catalyst. Subsequently the alkali metal-containing catalyst is treated in a substantially inert atmosphere at a temperature of at least 450° C. for a sufficient period at a steady state to reactivate the catalyst.

The substantially inert atmosphere is one that is substantially free of oxidizing gases such as oxygen.

The catalyst is preferably made by impregnating a porous support, preferably having a surface area in the range of 0.2 to 2.0 m$^2$/g, with a hydrocarbon solution of a silver salt of a neo-acid having 7 or more carbon atoms. The solution should be substantially free of water and neo-acid as this aspect has been shown to be especially beneficial to catalyst performance and hence preferred. The impregnated support is activated by heating for a period of time sufficient to produce an active catalyst. A sufficient amount of alkali metal promoters is used initially to depress the activity and selectivity of the catalyst prior to the critical heat treating step. Finally the alkali metal containing catalyst is heat treated at a temperature of at least 450° C. in an inert gaseous atmosphere for a period of time sufficient to reactivate the depressed catalyst.

Following the present invention, an improved ethylene oxide catalyst can be prepared from a silver salt of a neo-acid with a high temperature alkali treatment at a lower temperature for a short period of time, and become more active, and/or more selective, and/or more stable than an ethylene oxide catalyst prepared from the same silver salt of the same neo-acid but without the high temperature alkali treatment, or an ethylene oxide catalyst prepared with the same high temperature alkali treatment but from other silver salts.

The mechanism by which this is accomplished is not clear at the present time and forms no part of the invention. X-ray fluorescent examination of catalyst after heat treatment in air at 400 to 700° C. has indicated that heat treatment causes the alkali metal, e.g., cesium, to migrate, which is also believed to be the condition existing in commercial reactors. The information tends to point to the cesium migration as a principal problem. By supplying cesium in an excess of the amount which has been found to give the best catalyst, followed by heat treating may cause the cesium to migrate to all of the active sites at this time thereby tying up all of these sites before use in the oxidation process, thereby in effect immobilizing the Cs since there is nowhere else for it to go. The improved stability may be attributed to the immobilization of cesium and silver during the high temperature treatment. Additionally there may be a beneficial effect of the silver salts of neo-acids over other silver salts when all the catalysts have the same high temperature alkali treatment. It may involve a beneficial effect of the high temperature alkali treatment when all catalysts have used the same silver salt of a same neo-acid. It may also involve a synergistically beneficial effect of having a silver salt of a neo-acid and the high temperature alkali treatment together. More specifically, the improved activity and selectivity may be attributed to the highly dispersed fine silver particles derived from the silver salt of a neo-acid. The crystallite sizes of the silver particles on the catalysts prepared in the present invention, measured by x-ray diffraction method, have been found to be 50–1000 A, usually 100–500 A.

DETAILED DESCRIPTION AND PREFERRED EMBODIMENT

The supports in general may be any of a wide variety of materials which possess the proper surface area and porosity and which do not catalyze the combustion of either ethylene or ethylene oxide when coated with silver under reaction conditions. Suitable supports have been found to be alumina, silica, silica-alumina, silicon carbide or combinations thereof. Preferred supports are those containing principally alpha-alumina, particularly those containing up to about 15 wt. % silica. The supports may be in any suitable physical form, e.g., spheres, rings, granules, etc. The amount of silver deposited hereon is generally in the range of 3–25%, preferably 5–20%, and desirably 7–15% by weight.

The supports in general should have a low surface area of 0.2 to 2 $m^2/g$, preferably 0.4 to 1.6 $m^2/g$, and most preferably 0.5 to 1.3 $m^2/g$ The pore volume of the support should be in the range of 0.1 to 1.0 cc/g, preferably 0.2 to 0.5 cc/g. The median pore diameter of the support should generally be in the range of 0.1 to 50 microns, preferably 0.5 to 20 microns, and desirably 1 to 10 microns. The supports may contain alkali and alkaline earth elements up to 1%, but preferably no more than to 0.5%, desirably no more than to 0.3%.

The catalysts described in-the examples were made on the following supports (Table I) obtained from the Norton Company and Noritake, Inc.

TABLE I

| Support Sample | Surface Area ($m^2/g$) | Pore Volume (cc/g) | Medium Pore Diameter (Micron) | Sodium Content Wt. % $Na_2O$ |
|---|---|---|---|---|
| A Noritake | 0.85–0.95 | 0.30–0.40 | 1.0–2.5 | 0.23–0.26 |
| B Norton | 0.55–0.65 | 0.28–0.35 | 1.0–2.0 | 0.09–0.12 |

To produce a catalyst according to the present invention, the support material is preheated to 85° C. for 30 minutes and then placed in the silver solution until all of the solution is absorbed by the support. Preferably the quantity of said silver solution used to impregnate said porous support is no more than is necessary to fill the pore volume of said porous support, for example, by impregnating a porous support having a surface area of between 0.2 and 2.0 $m^2/g$ with an organic solution silver salt of neo-acid having 7 carbon atoms sufficient to provide 3 to 25 wt. % silver on the support, the quantity of said organic solution being no more than is necessary to fill the pore volume of said support. The saturated support is then activated by placing it in an oven for 0.1 to 5 hours at 250° to 500° C. Alternatively, the impregnated support may be placed on a moving wire-mesh belt and passed through a hot zone where it is exposed for about 0.1 to 5 minutes, preferably 0.4 to 3, desirably 0.7 to 2 minutes to an upward flowing stream of air having a temperature of 350° to 600° C., preferably 400° to 550° C.

Although various alkali metals have been used as promoters, Na, K, Cs and Rb are preferred with Cs and Rb being found most useful. Cesium is the preferred alkali metal.

After cooling to room temperature, the catalyst is impregnated with a solution of alkali metal, e.g., cesium compound, such as a hydroxide or salt, in a water-ethanol mixture and dried to obtain 500 to 15000 ppm, preferably 650 to 8000 ppm, desirably 800 to 5000 ppm cesium by saturating the pores of the catalyst precursor. This solution can be prepared by diluting a concentrated aqueous cesium compound solution such as hydroxide, acetate, etc. with anhydrous ethanol. Preferably the quantity of the said cesium containing solution used to impregnate said activated catalyst is no more than is necessary to fill the pore volume of said activated catalyst, for example activated catalyst may be impregnated with an ethanol-water solution of cesium hydroxide sufficient to deposit from 650 to 8000 wppm cesium on said activated catalyst to provide a catalyst precursor, the quantity of said cesium hydroxide containing ethanol-water solution being no more than is necessary to fill the pore volume of said activated catalyst.

The cesium loading on the catalyst has been generally found to be proportional to the porosity of the catalyst as well as to the concentration of the diluted cesium solution. Practically, the porosity of the catalyst can be measured by the water absorption of the catalyst support used. Preferably the catalyst produced is one wherein the quantity of cesium on said catalyst after heat treatment is between 800-5000 wppm.

The high temperature treatment of the alkali containing catalysts is carried out at a temperature of at least 450° C., preferably higher than 500° C. and desirably higher than 550° C. in an inert gas such as nitrogen. The inert gas can be nitrogen, helium, argon, etc. or combinations thereof.

The high temperature treatment should be done for a period of time sufficient to reactivate the depressed catalysts. A steady-state period at the specified high temperature can be less than 8 hours, preferably less than 5 hours, and desirably less than 3 hours preferably 0.1 to 4.5 hours. The heat-up and cool-down periods are less critical to the catalyst than the steady-state period. Generally, the heat-up and cool-down periods are less than 4 hours, preferably less than 2.5 hours and desirably less than 1.5, more preferably from 0.25 to 1.5 hours.

Before heat-up, the high temperature treatment system including the alkali containing catalyst for the treatment preferably is purged with the specified gas for a period of time sufficient to completely replace the air in the system including the air in the pores of the catalyst. To assure a complete replacement of air, the flow rate of the specified gas during the purge period should be maintained at 1 to 20, preferably 3 to 12, desirably 5 to 8 liter per min. per 200 to 250 gram of catalyst with some positive delivery pressure e.g., 7 to 10 psig, preferably 7.5 to 9.5 psig. After the purge period, the flow rate of the specified gas can be reduced to start the heat-up period but the positive delivery pressure should be kept. The same flow rate and positive pressure as in the heat up period should be maintained throughout the steady-state period and the cool-down period.

In an an alternative procedure a reduced flow rate for the inert gas may be used, such as 10 to 15 cc per 200 to 250 grams of catalyst precursor at a pressure of about 2.0 to 4.0 psig.

In one embodiment in a sealed container the purging may continue during the heat up, e.g., the catalyst may be heated to about 600° C. over an hour while the purge continues, then to maintain the temperature at this steady state for about 10 to 45 minutes with continued purging.

For the purpose of high temperature treatment, the alkali containing catalyst may be put in a oven, a box furnace, a tube furnace, or a rotary kiln, fired by gas or electrically heated with or without a retort or a jacket. However, the heat treating apparatus should be capable of sealing and maintaining the desired atmosphere.

Catalysts prepared by the procedures described above have been shown to have improved performance for use in the vapor phase oxidation of ethylene with molecular oxygen to ethylene oxide. Oxidation reaction conditions usually involve reaction temperatures of 150°-400° C., preferably 200°-300° C., and reaction pressures of 0.1-3000 psig, preferably 100-1000 psig. The reactant feed mixtures usually contain 0.5-20% ethylene, 3-15% oxygen, with the balance comprising comparatively inert materials including nitrogen, carbon dioxide, methane, ethane, argon and the like. Reaction modifiers, usually halogen-containing compounds such as ethylene dichloride, vinyl chloride and the like, may be included in small amounts. In the production of ethylene oxide, only a portion of the ethylene usually is reacted per pass over the catalyst. After the separation of the desired ethylene oxide product and the removal of appropriate purge streams and carbon dioxide, unreacted material is usually returned to the reactor.

In the examples the catalysts are made from a cumene solution of a silver salt of neo-decanoic acid (NDA). The NDA may be obtained from Exxon Chemical Company. This solution is prepared by reacting silver oxide with NDA in cumene following the method disclosed in the Example 1 of U.S. Pat. No. 4,663,303, such patent being incorporated herein. A weight ratio of silver salt (silver neo-decanoate)/cumene solvent of 1/1 to 3.5/1 may be used, particularly about 2/1.

EXAMPLE 1

A silver neo-decanoate/cumene solution is prepared from 539.00 gm of neo-decanoic acid (obtained from Exxon Chemical Co.), 350.00 gm of cumene (obtained from Aldrich Chemical Co.), and an excessive amount of silver oxide (392.21 gm) in a similar manner to that described in Example 1 of U.S. Pat. No. 4,663,303. A 496.42 gm sample of this solution is diluted with 19.35 gm of cumene to yield a solution having a weight ratio of silver salt/cumene of 2.2/1.0.

A 660.21 gm sample of the Support A material (5/16"×5/16" ring with ⅛" wall, 0.85–0.95 $m^2$/g surface area, 0.30–0.40 cc/g pore volume, and 0.23–0.26 wt. % $Na_2O$) is preheated to 85° C. and impregnated with 271.92 gm of the 2.2/1.0 silver neo-decanoate/cumene solution at 80° C. for 30 minutes. The amount of solution used is predetermined as the amount which is exactly the solution which the support can absorb. That is, the volume of the solution equals the pore volume of the support sample.

The saturated support is activated by placing it on a moving wire-mesh belt and passing the impregnated support through a zone where it is exposed to an upward flowing stream of air having a temperature of 400° C. for about 1 minute. After cooling to room temperature, the catalyst is found to contain about 9.19 wt. % of silver and have a total weight of 727.04 gm.

A 232.24 gm sample of the belt-activated silver catalyst is impregnated with a solution of cesium hydroxide in a water-ethanol mixture containing about 9174 wt. ppm of cesium. The solution is prepared by mixing 1.05 gm of an aqueous cesium hydroxide solution containing about 50 wt % of CsOH, with about 49.58 gm of anhydrous ethanol. The amount of the solution (50.63 gm) is predetermined as the amount which the catalyst can absorb as described above. After the cesium impregnation at room temperature for about 10 minutes, the catalyst is dried to produce a catalyst precursor containing about 2000 wt. ppm of cesium.

The high temperature treatment of the alkali-containing catalyst precursor is carried out as follows. A 214 gm sample of the catalyst precursor is placed in a retort which is capable of an air tight seal. The retort is fitted into the chamber of an electric furnace. A stream of nitrogen is introduced into the retort. The nitrogen flows through the catalyst bed before leaving the retort. The system is initially purged with about 6 liter/min. of nitrogen at room temperature for 2 hours with a positive delivery pressure of about 7.5-9.5 psig. After the purge, the flow rate of the nitrogen is reduced to about 10 cc/min. with about 3 psig delivery pressure to start a 1 hour heat-up period. At the end of the heat-up period, the temperature is controlled at 600° C. for a steady-state period of 45 minutes. After the steady-state period, the heat supply of the furnace is turned off and the cool-down period starts. After cooling down to room temperature, the $N_2$ is stopped. The finished catalyst obtained after this high temperature treatment is designated "Catalyst 1-A" and found to contain 1248 wt. ppm cesium by analysis.

A charge of 36 gm of Catalyst 1-A was placed in a reactor consisting of ¼" stainless steel tube which is heated in a salt-bath. A feed mixture of 7% $O_2$, 8% $CO_2$, 15% $C_2H_4$, 70% $N_2$, and 0.6 ppm ethylene dichloride is passed over the catalyst with a gas space velocity of 5500 hr$^{-1}$. The pressure was maintained at 300 psig (21.69 bar) and the temperature between 200°–300° C. as required to obtain an outlet concentration of 1.5 vol. % ethylene oxide The results of the test are shown in Table II.

EXAMPLE 2

In order to demonstrate the importance of the amount of the alkali metals used in the high temperature treatment on the performance of a finished catalyst, two catalyst samples are prepared from the same Support A (Table I) and the same silver neo-decanoate/cumene solution that was used for Catalyst 1-A. The same procedures are used to prepare Catalyst 1-A as described in Example 1. However, different cesium loadings are used in the high temperature treatments.

"Catalyst 2-A" is impregnated with a 50.63 gm aqueous CsOH/ethanol solution containing 6881 ppm of cesium for a 232 gm of catalyst precursor and dried to obtain about 1500 wt. ppm of cesium before the high temperature treatment "Catalyst 2-B" is impregnated with 50.63 gm of an aqueous CsOH/ethanol solution, but containing 11468 ppm of Cs for a 232 gm of catalyst precursor and dried to obtain about 2500 ppm Cs before the high temperature treatment.

The conditions used in the high temperature treatment and the salt-bath reactor test for Catalysts 2-A and 2-B are the same as those used for Catalyst 1-A in Example 1. The reactor test results of Catalysts 2-A and 2-B are shown in Table II together with those of Catalyst 1-A.

TABLE II

| Catalyst | Cs Loading before High Temp. Treatment (ppm) | Cs Loading after High Temp. Treatment (ppm) | Hrs. on STM | Reactor Test Results Temp. (°C.) | EO (%) | Sel (%) |
|---|---|---|---|---|---|---|
| 1-A | 2000 | 1248 | 194 | 224 | 1.50 | 81.3 |
| 2-A | 1500 | 922 | 306 | 222 | 1.51 | 79.6 |
| 2-B | 2500 | 2031 | 148 | 232 | 1.49 | 81.5 |

EXAMPLE 3

A sufficient amount of a silver catalyst precursor is made from a silver neo-decanoate/cumene solution and Support B in Table I (0.55–0.65 m²/g Surface Area, 0.28 0.35 cc/g pore volume, 1.0–2.0 micron medium pore diameter, 0.09–0.12 wt. % $Na_2O$). The precursor is activated on a belt-dryer and impregnated with an aqueous CsOH/ethanol solution and dried to obtain about 1000 ppm cesium in a manner similar to that described in Example 1. This catalyst precursor is used as the starting material from which ten catalyst samples, designated as Catalysts 3-A thru 3-J, are prepared to demonstrate the critical effects of the temperature and the time of the steady-state period in the high temperature treatment on the performance of the finished catalysts.

The specific temperature and time of the steady-state period used for each catalyst sample is shown in Table III. The general conditions used in the hi9h temperature treatments and the salt-bath reactor tests were both the same as those used for Catalyst 1-A in Example 1. The reactor test results of Catalysts 3-A thru 3-J are also shown in Table III.

TABLE III

| Catalyst | Steady-State Condition in High Temp. Treatment Temp (°C.) | Time (hr) | Hrs. on STM | Reactor Test Results Temp (°C.) | EO (%) | Sel (%) |
|---|---|---|---|---|---|---|
| 3-A | 500 | 2 | 147 | 282 | 1.5 | 70.1 |
| 3-B | 525 | 2 | 189 | 246 | 1.5 | 79.1 |
| 3-C | 550 | 0.5 | 412 | 246 | 1.5 | 79.7 |
| 3-D | 550 | 2 | 479 | 243 | 1.5 | 80.3 |
| 3-E | 550 | 3 | 265 | 232 | 1.5 | 81.1 |
| 3-F | 550 | 4 | 336 | 233 | 1.5 | 81.3 |
| 3-G | 600 | 0.5 | 444 | 231 | 1.5 | 80.9 |
| 3-H | 600 | 2 | 622 | 227 | 1.5 | 81.7 |
| 3-I | 650 | 0.5 | 381 | 221 | 1.5 | 80.0 |
| 3-J | 700 | 0.5 | 154 | 220 | 1.5 | 76.1 |

As may be seen from the above test results, the catalysts prepared by the method of the present invention are all useful for the vapor-phase oxidation of ethylene to ethylene oxide.

EXAMPLE 4

To determine if the heat treatment method is as effective for different silver loading solution, a catalyst was prepared using a silver lactate solution in lieu of the neo-acid salt solution. The silver lactate solution was prepared according to the method disclosed in U.S. Pat. No. 4,774,222 which is hereby incorporated by reference. The catalyst support B was loaded with silver lactate and initially activated as in Example 1 above to give a catalyst having 8.3% silver. Three samples were then prepared having different cesium loadings. Each of the samples were then heat treated and tested as in Example 1. The results are shown in Table IV below.

TABLE IV

| Catalyst | Cs Loading before High Temp. Treatment (ppm) | Cs Loading after High Temp. Treatment (ppm) | Hrs. on STM | Reactor Test Results Temp. (°C.) | EO (%) | Sel (%) |
|---|---|---|---|---|---|---|
| 4A | 500 | not meas. | 187 | 248 | 1.5 | 77.1 |
| 4B | 1000 | not meas. | 245 | 265 | 1.5 | 74.2 |
| 4C | 1500 | 1407 | 187 | 300 | 1.5 | 61.1 |

As may be noted while the lower cesium loaded catalyst performed comparable to the neo-acid salt catalysts, the other two (4B & 4C) required considerably higher temperature to achieve the 1.5 % conversion. Additionally catalyst 4C exhibited significantly poorer selectivity. Thus, unexpectedly, the silver lactate prepared catalyst did not respond to the heat treatment method as well as the silver neo-acid salt prepared catalyst.

The invention claimed is:

1. A process for preparing a supported silver catalyst useful for the vapor-phase oxidation of ethylene to ethylene oxide, comprising the steps of:

(a) impregnating a porous support having a surface area of about 0.2 to 2.0 2/g with a hydrocarbon solution of a silver salt of a neo-acid containing at least seven carbon atoms sufficient to provide 3 to 25 wt % silver on the support, and separating the impregnated support from said solution;
(b) activating said impregnated support by heating in air for sufficient time to produce an active catalyst;
(c) impregnating said activated catalyst with a solution containing an alkali metal compound in an amount sufficient to provide an amount of said alkali metal to depress the activity and selectivity of said activated catalyst to produce a catalyst precursor, said alkali metal being selected from the group consisting of sodium, potassium, cesium, and rubidium, and
(d) heat treating said catalyst precursor in a substantially inert atmosphere at a temperature of between 450° and 700? C. for between 0.1 to 4.5 hours at a steady state to reactivate the precursor to produce an active catalyst.

2. The process of claim 1 wherein said impregnated support is activated by heating in air in an oven at a temperature in the range of 250° to 500° C. for about 0.1 to 5.0 hours.

3. The process of claim 1 wherein said impregnated support is activated by placing it on a moving wire mesh belt and passing it through a zone where it is exposed for about 0.1 to 5.0 min to an upward flowing stream of air having a temperature in the range of 350° and 600° C.

4. The process of claim 1 wherein said alkali metal is cesium.

5. The process of claim 4 wherein said cesium is contained in an ethanol-water solution as cesium hydroxide.

6. The process of claim 5 wherein the quantity of cesium containing solution used to impregnate said activated catalyst is no more than is necessary to fill the pore volume of said activated catalyst.

7. The process of claim 1 wherein the quantity of said silver solution used to impregnate said porous support is no more than is necessary to fill the pore volume of said porous support.

8. The process of claim 6 wherein the quantity of cesium on said catalyst precursor is 650 to 8000 wppm.

9. The process of claim 1 wherein said heat treatment comprises the steps of:
(a) placing the catalyst precursor in a sealed container;
(b) purging the catalyst in said container with an inert gas for a sufficient period of time to displace all of the air within said container and within said catalyst precursor;
(c) heating said catalyst in said container to about 600° C. over a period of about 1 hour while continued purging with said inert gas;
(d) controlling the temperature of said catalyst in said container at a steady state temperature of about 600° C. for 10 to 45 minutes while continuing said inert gas purge; and
(e) cooling down said catalyst to room temperature while continuing said inert gas purge.

10. The process of claim 9 wherein said inert gas is nitrogen and the purge rate of (c) is about 5.0 to 8.0 liters per minute per 200 to 250 grams of catalyst precursor.

11. The process of claim 10 wherein said purge is at 7 to 10 psig.

12. A process for preparing a supported silver catalyst useful for the vapor-phase oxidation of ethylene to ethylene oxide, comprising the steps of:
(a) impregnating a porous support having a surface area of between 0.2 and 2.0 m²/g with an organic solution of a silver salt of a neo-acid having seven carbon atoms sufficient to provide 3 to 25 wt % silver on the support, the quantity of said organic solution being no more than is necessary to fill the pore volume of said support;
(b) activating said impregnated support by heating in air for a sufficient time to produce an active catalyst;
(c) impregnating said activated catalyst with an ethanol-water solution of cesium hydroxide sufficient to deposit from 650 to 8000 wppm cesium on said activated catalyst to provide a catalyst precursor, the quantity of said cesium hydroxide containing ethanol-water solution being no more than is necessary to fill the pore volume of said activated catalyst;
(d) heat treating said catalyst precursor by
(i) placing said catalyst precursor in a sealed container and purging and said catalyst precursor in said container for about two hours with nitrogen at a first purge rate of from 5.0 to 8.0 liters per min per 200 to 250 grams of catalyst precursor at from 7.5 to 9.5 psig;
(ii) heating said catalyst precursor to a temperature of between 500 and 700° C. over 0.25 to 1.5 hours while purging with nitrogen at a second purge rate in the range of 10–15 cc per min per 200 to 250 grams at about 2.0 to 4.0 psig;
(iii) controlling the temperature of said catalyst in said container at a steady state temperature selected from a temperature in the range between 500° and 700° C. for between 0.1 and 4.5 hours depending on the temperature while continuing to purge at said second purge rate; and
(iv) cooling down said catalyst to room temperature while continuing said second purge rate.

13. A process for preparing a supported silver catalyst useful for the vapor-phase oxidation of ethylene to ethylene oxide, comprising the steps of:
(a) impregnating a porous support having a surface area of about 0.2 to 2.0 m/g, with a hydrocarbon solution of a silver salt of a neo-acid having 7 or more carbon atoms sufficient to provide 3–25 wt % silver on the support, and separating the impregnated support from said solution;
(b) activating said impregnated support by heating in air for sufficient time to produce an active catalyst;
(c) impregnating said activated catalyst with a solution containing an alkali metal compound in an amount sufficient to provide an amount of said alkali metal to depress the activity and selectivity of said activated catalyst to produce a catalyst precursor, said alkali metal being selected from the group consisting of sodium, potassium, cesium, and rubidium, and
(d) heat treating said catalyst precursor in a substantially inert atmosphere at a temperature of at least 450° C. for a sufficient period of time at a steady state to reactivate the precursor to produce an active catalyst.

14. The process of claim 9 wherein said alkali metal is cesium.

15. The process of claim 14 wherein said cesium is contained in an ethanol-water solution as cesium hydroxide.

16. The process of claim 15 wherein the quantity of cesium on said catalyst precursor is 650 to 8000 wppm.

17. The process of claim 16 wherein the quantity of cesium on said catalyst after heat treating is between 800 and 5000 wppm.

18. The process of claim 8 wherein the quantity of cesium on said catalyst after heat treating is between 800 and 5000 wppm.

* * * * *